(12) United States Patent
Kacirek

(10) Patent No.: US 10,021,878 B2
(45) Date of Patent: Jul. 17, 2018

(54) METHOD OF INCREASING THE TASTE OF EDIBLE PRODUCE

(71) Applicant: Raymond E. Kacirek, St. Charles, IL (US)

(72) Inventor: Raymond E. Kacirek, St. Charles, IL (US)

(73) Assignee: Greatest Garden Produce LLC, Chicago, IL (US)

(*) Notice: Subject to any disclaimer, the term of this patent is extended or adjusted under 35 U.S.C. 154(b) by 101 days.

(21) Appl. No.: 13/799,614

(22) Filed: Mar. 13, 2013

(65) Prior Publication Data

US 2014/0274718 A1 Sep. 18, 2014

(51) Int. Cl.
| | |
|---|---|
| *A01N 43/04* | (2006.01) |
| *A01N 65/00* | (2009.01) |
| *A01N 65/08* | (2009.01) |
| *C05F 11/00* | (2006.01) |
| *C05G 1/00* | (2006.01) |

(52) U.S. Cl.
CPC ............ *A01N 43/04* (2013.01); *A01N 65/00* (2013.01); *A01N 65/08* (2013.01); *C05F 11/00* (2013.01); *C05G 1/00* (2013.01)

(58) Field of Classification Search
None
See application file for complete search history.

(56) References Cited

U.S. PATENT DOCUMENTS

| | | | |
|---|---|---|---|
| 1,501,914 A | 7/1924 | Nikaido | |
| 3,096,171 A | 7/1963 | Woerther | |
| 6,602,824 B1 * | 8/2003 | Miles et al. | 504/150 |
| 2012/0255335 A1 | 10/2012 | Fairweather et al. | |

FOREIGN PATENT DOCUMENTS

DE 102009024423 12/2010

OTHER PUBLICATIONS

Tomato Chronicles. Internet Date: 2010. Retrieved from the Internet: <URL: http://www.tomatocasual.com/2010/07/15/the-tomato-chronicles-diy-fertilizer/>.*
Fertilizing Tomatoes. Internet date: 2007. Retrieved from the Internet: <URL: http://backyardgranger.blogspot.com/2007/07/fertilizing-tomatoes.html>.*
FertilizerToIncreaseYield. Internet Archive Date: Feb. 7, 2011. Retrieved from the Internet: <URL: http://web.archive.org/web/20110207002233/http:/sites.google.com/site/fertilizertoincreaseyields/>.*
2006 http://perrone.blogs.com/horticultural/2006/08/why_arent_these.html.*
SFGate 2012 https://web.archive.org/web/20120801033923/http://homeguides.sfgate.com/pepper-fruit-growth-fertilizer-35670.html.*
"MG Organic Liquid Fertilizer Made From Sugar Beets", printed Feb. 7, 2013; http://www.forum.Grasscity.com/organic-growing/919621-mg-organic-liquid- . . . ; (4 pages).
Conrad, Jamie, "The Best Liquid Fertilizers for Vegetables"; printed Feb. 7, 2013; http://www.ehow.com/list_7609981_liquid-organic-fertilizers-vegetab . . . ; (3 pages).
Sloan, Christina, "How to Use Molasses As a Fertilizer"; printed Mar. 7, 2013; http://www.ehow.com/how_8100076_use-molasses-fertilizer.html (3 pages).
Patterson, Susan, "Molasses as Fertilizer: Information on Feeding Plants with Molasses"; printed Mar. 7, 2013; http://www.gardeningknowhow.com/garden-how-to/soil-fertilizers/feeding-plants-with-molasses.htm (2 pages).
Wiki.answers.com; "How Does Molasses Make Plant Blooms Bigger?", printed Mar. 7, 2013; http://wiki.answers.com/Q/How-does-molasses-make-blooms-bigger (6 pages).

* cited by examiner

*Primary Examiner* — Terry A McKelvey
*Assistant Examiner* — Catheryne Chen
(74) *Attorney, Agent, or Firm* — Pauley Erickson & Kottis

(57) ABSTRACT

The use of sugar beet extract, particularly sugar beet molasses, when applied to produce as a fertilizer or fertilizer supplement after flowering produces produce having improved sweetness and taste.

16 Claims, No Drawings

METHOD OF INCREASING THE TASTE OF EDIBLE PRODUCE

CROSS REFERENCE TO RELATED APPLICATIONS

None

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

This invention relates to a method of improving the taste and sweetness of edible produce. More particularly, this invention relates to improving the sweetness of vegetables and fruits.

2. Description of the Background of the Invention

There are a wide number of reasons that home gardeners plant gardens. Control of what is used to grow the produce, avoiding the use of pesticides and other chemicals for instance, is one reason given by home gardeners. A further reason is that home gardeners believe their home grown produce tastes better and is fresher than commercially available produce. Lastly, there is the recreational or hobby aspect to home gardening; people just enjoy gardening and collecting the fruits of their labors.

It has been known to use various carbohydrate compositions like sugar cane molasses or sugar beet molasses as either a fertilizer or as an insect deterrent product. In this regard there are either liquid or dry products that enable the use of these carbohydrate products on home grown products.

SUMMARY OF THE INVENTION

The method of the present invention relates to enhancing the flavor of edible produce by applying an effective amount of a sugar beet extract to the edible produce after the edible produce has flowered.

DETAILED DESCRIPTION OF THE PREFERRED EMBODIMENTS

Molasses is generally a by-product of extracting sugar from sugar cane, sugar beets or grapes. As the sugar containing material is mashed, ground up or boiled, a dark, sweet liquid is typically expelled. Depending on the source of the molasses or the stage of extraction, the resulting product is used as a food stuff for humans, animal feed, or an industrial feed stock.

Any sugar beet extract can be used in the method of the present invention. This includes first molasses, second molasses, un-sulfured molasses, sulfured molasses and blackstrap molasses. In sugar beet production, these are also called high green and low green. The final sugar is the only extract that is called molasses. Typical sugar beet extracts have some nitrogen, and phosphorous along with other nutrients and vitamins like potash, sulfur, calcium, magnesium iron and some potassium. A typical nutrient content for fertilizers of sugar beet extracts are 1-0-5, 6-0-0 and 8-0-0. Some sugar beet extracts may contain trace minerals that may make the material unsuitable for use as a human food source. However, because plants benefit from these trace materials, these non-food grade materials can also be used in the method of the present invention. One source of commercially available sugar beet extract is Midwest Agri, Minneapolis, Minn.

The sugar beet extract can be applied mixed with water or applied in a dried form that is available where the sugar beet product is dried on a carrier, such as a grain, bean or rice. When the extract is mixed with water it is typically applied at about one half to two ounces of extract per gallon of water and preferably from about 0.75 to 1.25 ounces of extract per gallon of water. This water mixture is then applied to the plants at a rate of about 0.5 to 4 quarts per plant and preferably about 1 to 2 quarts per plant. While the above amounts are typical, an application at a rate that produces the desired effect is contemplated. The extract can be applied directly to the soil around the plants or to the foliage.

The timing of the initial application of the extract is important. The first application of the extract to the plant should be after the plant has initially flowered. In one embodiment of the present invention, only a single application of the sugar beet extract is applied to the plants. In a second embodiment, one or more additional treatments at the same rate of application can be applied to the plants subsequently. These subsequent treatments are typically begin about one week after the initial treatment and if multiple added treatments are contemplated are applied at one week intervals thereafter until harvest.

So that the plants have adequate nutrition, a supplemental fertilizer can be applied to the plants prior to flowering and may either continue to be applied or discontinued after the time of flowering. Any commercially available fertilizer that is suitable for the plants being cultivated can be used. The fertilizer can be either in dry or liquid form for application to the plants. The fertilizer should be applied according to the package directions.

A wide variety of produce can be improved using the method of the present invention. The examples show select varieties of cantaloupe, bell pepper and tomatoes. Other similar produce can benefit from the method of the present invention.

The method of the invention will now be illustrated by the following examples. These examples should not be viewed as limiting the scope of the present invention.

EXAMPLE 1

Application to melons. A broadcast fertilizer treatment was applied prior to transplanting to provide initial fertility. The fertilizer was applied at a rate of 6 tablespoons of 13-13-13 fertilizer/20 ft. research plot (in 2012 the plot was 8 ft). The varieties of melons as set out in Table 1 were transplanted 2 feet apart in row spacing (10 plants to a plot) (in 2012 the spacing is 1.5 ft. giving 6 plants to a plot). As a control, the recommend amount of Miracle Grow Liquid Fertilizer (Trademark of The Scotts Company LLC) every week throughout the growing season. Use recommended liquid application of Miracle Grow fertilizer until fruiting, then apply only the sugar beet molasses product at a rate of 3 tablespoons per gallon to the roots of the plants and also to the leaves as well. This was done initially and then 1 time per week thereafter until harvest). For each experiment, there were randomized placement of the treatments and the experiment was replicated 4 times.

TABLE 1

|  | Year | Cantaloupe Variety | Ave. Wt.[1] | Soluble Solids[2] | Taste[3] |
|---|---|---|---|---|---|
| Control | 2009 | 'Athena' cultivar | 5.9 | 11.5 | 6.9 |
|  | 2010 | 'Cresent Moon' cultivar | 7.1 | 8.3 | 4.9 |
|  | 2011 | 'Fastbreak' cultivar | 4.8 | 8.0 | 5.2 |
|  | 2012[4] | 'Athena' cultivar | 3.1 | 7/10-13.2 7/17-10.7 | 7/10-5.8 7/17-4.4 |
| Example 1 | 2009 | 'Athena' cultivar | 5.8 | 13.3 | 7.6 |
|  | 2010 | 'Cresent Moon' cultivar | 7.5 | 10.0 | 6.5 |
|  | 2011 | 'Fastbreak' cultivar | 4.7 | 9.6 | 6.3 |
|  | 2012[4] | 'Athena' cultivar | 3.2 | 7/10-13.3 7/17-11.2 | 7/10-7.6 7/17-7.0 |

[1]Average weight of the fruit produced.
[2]Solids were measured using a hand-held refractometer on 3 fruit per plant at several times during growing season.
[3]Taste (Blind taste panel evaluated and rated the fruit for sweetness, with 1-3 = poor sweetness, 4-6 = some sweetness, and 7-9 = high sweetness of fruit).
[4]Dates of the tests were July 10 and July 17.

Using the method of the present invention, the yields of the plants were similar however, both the sugar content (measured by soluble solids) and the taste were improved using the method of the present invention. Because the sample size was small, the only statistically significant results were in 2010 and 2012 where both the sweetness and taste were significantly better, except for the Jul. 10, 2012 sweetness levels. The other two years the results showed directional improvement but the results were not statistically significant.

EXAMPLE 2

Application to bell peppers. A broadcast fertilizer treatment was applied prior to transplanting to provide initial fertility. The fertilizer was applied at a rate of 6 tablespoons of 13-13-13 fertilizer/10 ft. research plot. The varieties of peppers as set out in Table 1 were transplanted 2 feet apart in row spacing (10 plants to a plot). As a control, the recommend amount of Miracle Grow Liquid Fertilizer (Trademark of The Scotts Company LLC) every week throughout the growing season. Use recommended liquid application of Miracle Grow fertilizer until fruiting, then apply only the sugar beet molasses product at a rate of 3 tablespoons per gallon to the roots of the plants and also to the leaves as well. This was done initially and then 1 time per week thereafter until harvest). For each experiment, there were randomized placement of the treatments and the experiment was replicated 4 times.

TABLE 2

|  | Year[1] | Pepper Variety | Ave. Wt.[2] | Soluble Solids[3] | Taste[4] |
|---|---|---|---|---|---|
| Control | 2009 Early | 'Alliance' cultivar | 0.39 | 4.9 | 5.3 |
|  | 2009 Late | 'Alliance' cultivar |  | 5.7 | 6.1 |
|  | 2010 Early | 'Aristotle' cultivar | 0.29 | 5.8 | 6.0 |
|  | 2010 Late | 'Aristotle' cultivar |  | 6.3 | 5.4 |
|  | 2011[5] | 'Aristotle' cultivar | 0.28 | H3-7.3 H4-6.9 H5-7.2 H7-7.1 | ND |
|  | 2012[6] | 'Revolution' cultivar | 0.09 | 7/17-5.3 8/21-6.7 9/15-6.4 | 7/17-1.5 8/21-1.0 9/15-1.8 |
| Example 2 | 2009 Early | 'Alliance' cultivar | 0.37 | 4.9 | 7.3 |
|  | 2009 Late | 'Alliance' cultivar |  | 5.4 | 7.3 |
|  | 2010 Early | 'Aristotle' cultivar | 0.29 | 6.6 | 6.8 |
|  | 2010 Late | 'Aristotle' cultivar |  | 8.2 | 6.9 |
|  | 2011 | 'Aristotle' cultivar | 0.29 | H3-7.8 H4-7.0 H5-8.2 H7-8.2 | ND |
|  | 2012[6] | 'Revolution' cultivar | 0.13 | 7/17-6.3 8/21-5.7 9/15-6.9 | 7/17-3.5 8/21-3.0 9/15-3.8 |

[1]For 2009 and 2010 tests were done "early" (second pepper harvest) and "late" (next to last harvest of season).
[2]Average weight of the fruit produced.
[3]Solids were measured using a hand-held refractometer on 3 fruit per plant at several times during growing season.
[4]Taste (Blind taste panel evaluated and rated the fruit for sweetness, with 1-3 = poor sweetness, 4-6 = some sweetness, and 7-9 = high sweetness of fruit).
[5]For 2011 taste tests were not done but sweetness was measured after the $3^{rd}$, $4^{th}$, $5^{th}$ and $7^{th}$ harvests (H3, etc.).
[6]Dates of the test were July 17, August 21 and September 15.

Using the method of the present invention, the yields of the plants were similar however, both the sugar content (measured by soluble solids) and the taste were improved using the method of the present invention. Because the sample size was small, although the results show directional improvement for 2009-2011, the results were not statistically significant. For 2012 (a year when there was a drought), the method of the present invention produced produce that was significantly better in terms of sweetness and taste. Also, the size of the produce was significantly larger such that almost 15% more produce was of marketable size.

EXAMPLE 3

Application to tomatoes. A broadcast fertilizer treatment was applied prior to transplanting to provide initial fertility. The fertilizer was applied at a rate of 6 tablespoons of 13-13-13 fertilizer/6 ft. research plot. The varieties of tomatoes as set out in Table 3 were transplanted 2 feet apart in row spacing (3 plants to a plot). As a control, the recommend amount of Miracle Grow Liquid Fertilizer (Trademark of The Scotts Company LLC) every week throughout the growing season. Use recommended liquid application of Miracle Grow fertilizer until fruiting, then apply only the sugar beet molasses product at a rate of 3 tablespoons per gallon to the roots of the plants and also to the leaves as well. This was done initially and then 1 time per week thereafter until harvest). For each experiment, there were randomized placement of the treatments and the experiment was replicated 4 times.

TABLE 3

|  | Year | Tomatoe Variety | Ave. Wt.[1] | Soluble Solids[2] | Taste[3] |
|---|---|---|---|---|---|
| Control | 2012 | 'Phoenix' cultivar | 0.42 | 7/22-4.3 7/30-3.7 8/6-4.3 8/30-4.2 | 7/22-5.1 7/30-4.6 8/6-2.2 8/30-4.3 |

TABLE 3-continued

| | Year | Tomatoe Variety | Ave. Wt.[1] | Soluble Solids[2] | Taste[3] |
|---|---|---|---|---|---|
| Example 3 | 2012 | 'Phoenix' cultivar | 0.43 | 7/22-5.7<br>7/30-5.1<br>8/6-5.0<br>8/30-5.5 | 7/22-5.3<br>7/30-5.0<br>8/6-4.7<br>8/30-4.8 |

[1]Average weight of the fruit produced.
[2]Solids were measured using a hand-held refractometer on 3 fruit per plant at several times during growing season. Dates of the test were July 22, July 30, August 6 and August 30.
[3]Taste (Blind taste panel evaluated and rated the fruit for sweetness, with 1-3 = poor sweetness, 4-6 = some sweetness, and 7-9 = high sweetness of fruit).

Using the method of the present invention, the yields of the plants were similar however, both the sugar content (measured by soluble solids) and the taste were improved using the method of the present invention. Because the sample size was small, although the results show directional improvement for 2012, in most instances the results were not statistically significant (the only significant difference was for the August 6 taste that showed a significant improvement using the method of the present invention. For 2012 (a year when there was a drought), the size of the produce was significantly larger such that almost 15% more produce was of marketable size.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A method of enhancing a flavor of edible produce comprising:
   discontinuing applications of one or more complete soil fertilizers once the plant has flowered and through harvest of the edible produce;
   applying as an initial application an effective amount of a molasses derived from sugar beets and mixed in water to foliage and flowers of a plant producing the edible produce after the plant has flowered and before the edible produce has been harvested;
   applying a further effective amount of the molasses to the foliage and flowers of the plant approximately one week following the initial application;
   wherein application of the molasses results in enhancing flavor of the edible produce.

2. The method of claim 1 wherein the edible produce is cantaloupe, bell pepper or tomato.

3. The method of claim 1, further comprising:
   applying a second effective amount of the molasses to roots of the plant during the initial application; and
   applying a further second effective amount of the molasses to the roots approximately one week following the initial application.

4. The method of claim 1, further comprising:
   applying a liquid fertilizer to roots of the plant prior to flowering; and
   applying only the effective amount of the molasses to the plant after the plant has flowered.

5. The method of claim 1, wherein the effective amount of the molasses is applied only to the foliage and flowers of the plant after the plant has flowered.

6. The method of claim 1, wherein about 0.5 to 2 ounces of the molasses are mixed per gallon of the water for the initial application.

7. The method of claim 6, further comprising applying the molasses mixed with the water at a rate of about 0.5 to 4 quarts per plant during the initial application.

8. The method of claim 6, further comprising applying the molasses mixed with the water at a rate of about 1 to 2 quarts per plant during the initial application.

9. A method of enhancing a flavor of edible produce, comprising:
   applying more than one application of a complete soil fertilizer to a plant producing the edible produce before the plant flowers;
   discontinuing application of the complete soil fertilizer upon plant flowering and until all of the edible produce has been harvested from the plant;
   applying as an initial application an effective amount of a molasses derived from sugar beets and mixed in water to foliage and flowers of the plant after the plant has flowered and before the edible produce has been harvested;
   applying a further effective amount of the molasses to the foliage and flowers of the plant approximately one week following the initial application;
   repeatedly applying weekly applications of the further effective amount to the foliage and flowers until all of the edible produce has been harvested from the plant;
   wherein application of the molasses increases sugar content of the edible produce and results in enhancing flavor of the edible produce.

10. The method of claim 9, further comprising:
    applying a second effective amount of the molasses to roots of the plant during the initial application; and
    repeatedly applying weekly root applications of the second effective amount of the molasses to the roots until all of the edible produce has been harvested from the plant.

11. The method of claim 10, wherein about 0.5 to 2 ounces of the molasses are mixed per gallon of the water for the weekly applications and the weekly root applications.

12. The method of claim 11, further comprising applying the molasses mixed with the water at a rate of about 0.5 to 4 quarts per plant for the weekly applications and the weekly root applications.

13. The method of claim 11, further comprising applying the molasses mixed with the water at a rate of about 1 to 2 quarts per plant for the weekly applications and the weekly root applications.

14. The method of claim 9, wherein the effective amount of the molasses is applied only to the foliage and flowers of the plant after the plant has flowered.

15. The method of claim 14, wherein about 0.5 to 2 ounces of the molasses are mixed per gallon of the water for the initial application.

16. The method of claim 15, further comprising applying the molasses mixed with the water at a rate of about 1 to 2 quarts per plant during the initial application.

* * * * *